/ / / US011213188B2

United States Patent
Tosaka et al.

(10) Patent No.: US 11,213,188 B2
(45) Date of Patent: Jan. 4, 2022

(54) OPTICAL FIBER SCANNING DEVICE, OPTICAL SCANNING TYPE ENDOSCOPE AND ENDOSCOPE SYSTEM

(71) Applicant: OLYMPUS CORPORATION, Tokyo (JP)

(72) Inventors: Hiroshi Tosaka, Nagano (JP); Masanori Ogata, Matsumoto (JP)

(73) Assignee: OLYMPUS CORPORATION, Tokyo (JP)

( * ) Notice: Subject to any disclaimer, the term of this patent is extended or adjusted under 35 U.S.C. 154(b) by 716 days.

(21) Appl. No.: 16/045,970

(22) Filed: Jul. 26, 2018

(65) Prior Publication Data

US 2018/0325362 A1 Nov. 15, 2018

Related U.S. Application Data

(63) Continuation of application No. PCT/JP2016/052507, filed on Jan. 28, 2016.

(51) Int. Cl.
| | |
|---|---|
| *G02B 26/08* | (2006.01) |
| *A61B 1/00* | (2006.01) |
| *G02B 26/10* | (2006.01) |
| *A61B 1/04* | (2006.01) |
| *A61B 1/07* | (2006.01) |

(52) U.S. Cl.
CPC ...... *A61B 1/00172* (2013.01); *A61B 1/00006* (2013.01); *A61B 1/00096* (2013.01); *A61B 1/00165* (2013.01); *A61B 1/042* (2013.01); *A61B 1/07* (2013.01); *G02B 26/10* (2013.01); *G02B 26/103* (2013.01)

(58) Field of Classification Search
CPC . A61B 1/00172; A61B 1/042; A61B 1/00165; A61B 1/00096; A61B 1/00006; A61B 1/07; G02B 26/103; G02B 26/10

USPC ........................................................ 359/200.7
See application file for complete search history.

(56) References Cited

U.S. PATENT DOCUMENTS

| | | |
|---|---|---|
| 2009/0015894 A1 | 1/2009 | Rosman et al. |
| 2018/0153382 A1* | 6/2018 | Ogata ............... G02B 23/26 |

FOREIGN PATENT DOCUMENTS

| | | |
|---|---|---|
| EP | 1901107 A1 | 3/2008 |
| JP | 2008116922 A | 5/2008 |
| JP | 2014081484 A | 5/2014 |

(Continued)

OTHER PUBLICATIONS

International Search Report dated Apr. 26, 2016 issued in PCT/JP2016/052507.

*Primary Examiner* — Euncha P Cherry
(74) *Attorney, Agent, or Firm* — Scully, Scott, Murphy & Presser, P.C.

(57) ABSTRACT

An optical fiber scanning device includes a housing, an optical fiber configured to emit light, a magnet disposed on the optical fiber, four drive coils configured to drive the optical fiber by applying to the magnet a magnetic field generated by a received drive power signal, and four detection coils configured to output an induced electromotive force signal corresponding to variation of a magnetic field, wherein the drive power signal is controlled based on the induced electromotive force signal, and four coil assemblies each including any one of the drive coils and any one of the detection coils are disposed at rotationally symmetrical positions so as to interpose the optical fiber among the four coil assemblies.

14 Claims, 12 Drawing Sheets

(56) References Cited

FOREIGN PATENT DOCUMENTS

| | | |
|---|---|---|
| JP | 2015211761 A | 11/2015 |
| WO | 2014061354 A1 | 4/2014 |
| WO | 2015166743 A1 | 11/2015 |

\* cited by examiner

OPTICAL FIBER SCANNING DEVICE, OPTICAL SCANNING TYPE ENDOSCOPE AND ENDOSCOPE SYSTEM

CROSS REFERENCE TO RELATED APPLICATION

This application is a continuation application of PCT/JP2016/052507 filed on Jan. 28, 2016, the entire contents of which are incorporated herein by this reference.

BACKGROUND OF INVENTION

1. Field of the Invention

The present invention relates to an optical fiber scanning device that includes a detection coil configured to output an induced electromotive force signal corresponding to variation of a magnetic field, and controls a drive power signal based on the induced electromotive force signal, an optical scanning type endoscope including the optical fiber scanning device at a rigid distal end portion of an insertion section of the optical scanning type endoscope, and an endoscope system including the optical scanning type endoscope.

2. Description of the Related Art

An image pickup apparatus using an image pickup device such as a CCD or a CMOS image sensor simultaneously receives reflected light from a subject by multiple light receiving elements arranged in a matrix form to acquire a subject image. In the case of an endoscope configured to photograph a dark inside of a body, an image in a range illuminated with light from a light source is acquired.

On the other hand, as for an image pickup apparatus including an optical fiber scanning device, a subject is irradiated and scanned with a light spot and reflected light from the subject is sequentially received by one light receiving element so as to create a subject image based on light reception data of the reflected light.

Japanese Patent Application Laid-Open Publication No. 2008-116922 discloses an optical fiber scanning device using magnetic force. In this optical fiber scanning device, an optical fiber having a magnet disposed on the optical fiber is arranged along a center axis of a magnetic field generating unit including a drive coil and a sensor coil arranged so as to face each other in a cylinder. Position information of the magnet, that is, a scanning state of the optical fiber is detected based on variation of a magnetic field detected by the sensor coil, and a drive signal to the drive coil is subjected to feedback control.

Note that Japanese Patent Application Laid-Open Publication No. 2014-81484 discloses an optical fiber scanning device equipped with a drive coil including a planar spiral coil formed on a board.

SUMMARY OF THE INVENTION

An optical fiber scanning device according to an embodiment includes: a housing having a cylindrical shape; an optical fiber that is arranged along a center axis of the housing and configured to emit light from a free end of the optical fiber; a magnet disposed on the optical fiber; four drive coils that are disposed in the housing and configured to drive the free end of the optical fiber by applying, to the magnet, a magnetic field generated by a received drive power signal; and four detection coils that are disposed in the housing and configured to output an induced electromotive force signal corresponding to variation of a magnetic field, wherein the drive power signal is controlled based on the induced electromotive force signal, and four coil assemblies each including any one of the drive coils and any one of the detection coils are disposed at rotationally symmetrical positions so as to interpose the optical fiber among the four coil assemblies.

An optical scanning type endoscope according to another embodiment includes an optical fiber scanning device at a rigid distal end portion of an insertion section, wherein the optical fiber scanning device includes: a housing having a cylindrical shape; an optical fiber that is arranged along a center axis of the housing and configured to emit light from a free end of the optical fiber; a magnet disposed on the optical fiber; four drive coils that are disposed in the housing and configured to drive the free end of the optical fiber by applying, to the magnet, a magnetic field generated by a received drive power signal; and four detection coils that are disposed in the housing and configured to output an induced electromotive force signal corresponding to variation of a magnetic field, the drive power signal is controlled based on the induced electromotive force signal, and four coil assemblies each including any one of the drive coils and any one of the detection coils are disposed at rotationally symmetrical positions so as to interpose the optical fiber among the four coil assemblies.

An endoscope system according to another embodiment includes: an optical scanning type endoscope including an optical fiber scanning device; a power supply configured to output a drive power signal; a correcting circuit configured to output a correction signal in which influence on induced electromotive force by a magnetic field generated by a drive coil is cancelled from an induced electromotive force signal; and a controller configured to control the power supply based on the correction signal, wherein the optical fiber scanning device includes: a housing having a cylindrical shape; an optical fiber that is arranged along a center axis of the housing and configured to emit light from a free end of the optical fiber; a magnet disposed on the optical fiber; four drive coils that are disposed in the housing and configured to drive the free end of the optical fiber by applying, to the magnet, a magnetic field generated by a received drive power signal; and four detection coils that are disposed in the housing and configured to output an induced electromotive force signal corresponding to variation of a magnetic field, the drive power signal is controlled based on the induced electromotive force signal, and four coil assemblies each including any one of the drive coils and any one of the detection coils are disposed at rotationally symmetrical positions so as to interpose the optical fiber among the four coil assemblies.

DETAILED DESCRIPTION OF THE PREFERRED EMBODIMENTS

First Embodiment

An optical fiber scanning device 10 of a present embodiment will be described. Note that in the following description, drawings for each embodiment are schematic, and thus the relationship between thickness and width of each portion, the ratio in thickness of respective portions, etc. are different from the actual ones. In some cases, portions having different dimensional relationship and ratios among the drawings may be contained. In addition, illustrations and representations of some components by reference signs may be omitted.

Figure 1:
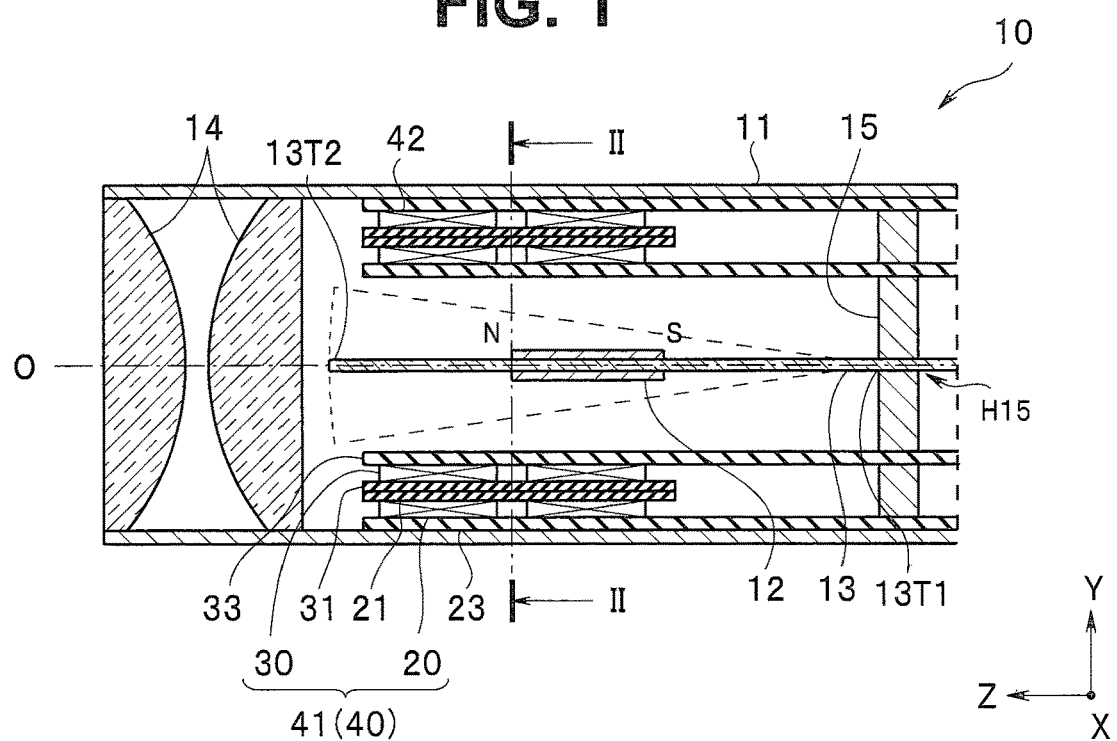
FIG. 1 is a cross-sectional view along a center axis of an optical fiber scanning device according to a first embodiment.
Figure 2:
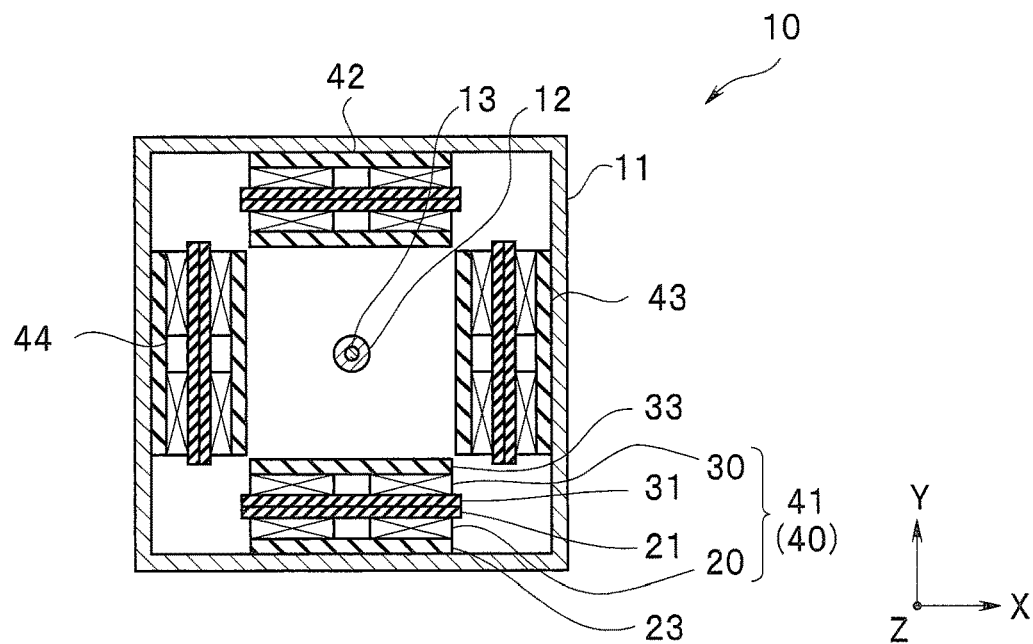
FIG. 2 is a cross-sectional view along II-II line of FIG. 1 of the optical fiber scanning device according to the first embodiment.

As shown in FIGS. 1 and 2, the optical fiber scanning device 10 includes a housing 11 having a cylindrical shape, an optical fiber 13, a magnet 12 disposed on the optical fiber 13, coil assemblies 41 to 44, and an illumination optical system 14. The optical fiber 13 is arranged along a center axis O (Z-axis direction) of the housing 11.

The housing 11 is formed of nonmagnetic metal such as aluminum or resin. The housing 11 having a cylindrical shape includes a hollow portion having a square cross-section (XY plane) orthogonal to the center axis O. For example, the housing 11 has an outer shape ranging from not less than 1 mm to not more than 10 mm, and a wall thickness, for example, ranging from not less than 10 µm to not more than 1000 µm. The housing may be a cube having an outer surface corner portions which are subjected to curved surface processing/chamfering, or may have a circular shape.

The optical fiber 13 guides light from a light source unit (not shown), and emits illumination light from a free end 13T2. The illumination light is applied to a subject in the form of a spot through an illumination optical system 14 including plural lenses.

For example, the magnet 12 formed of SmCo alloy is a cylindrical type, and magnetized in a longitudinal axis direction (optical-axis direction: Z-axis direction). The optical fiber 13 is inserted through a through-hole H15 of a holding member (ferrule) 15 and joined. A cantilevered free end 13T2 of the optical fiber 13 in which a joint portion (fixed end 13T1) to the holding member 15 is fixed is movable in an up-and-down direction and a right-and-left direction within the XY plane with the fixed end 13T1 as a base point.

The four coil assemblies 41 to 44 are disposed at rotationally symmetrical positions inside the housing 11 so as to interpose the optical fiber 13 among the four coil assemblies 41 to 44. Note that each of the coil assemblies 41 to 44 will be hereunder referred to as a coil assembly 40.

Figure 3:
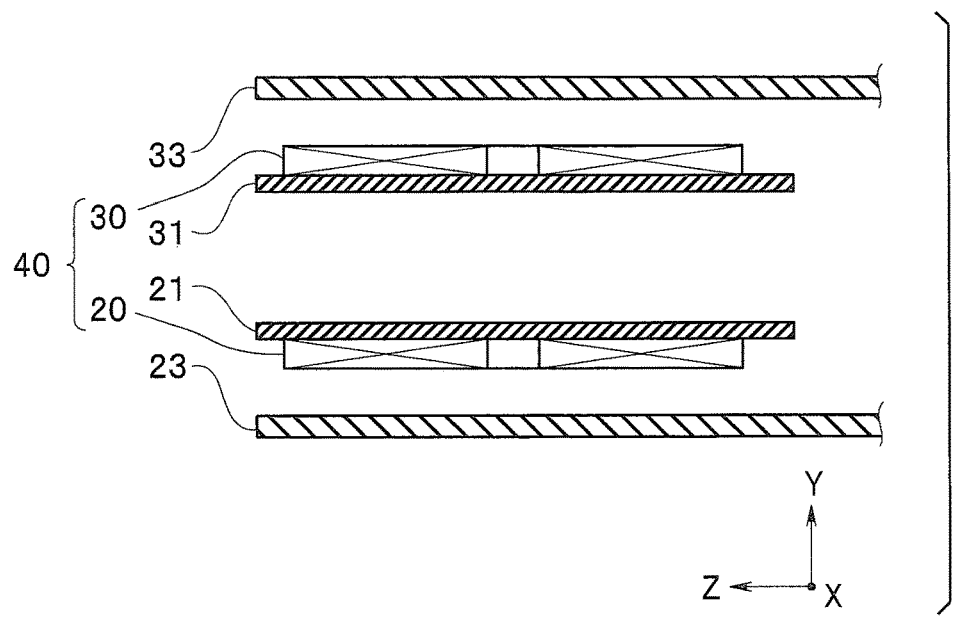
FIG. 3 is an exploded view of a coil assembly of the optical fiber scanning device of the first embodiment.
Figure 4A:
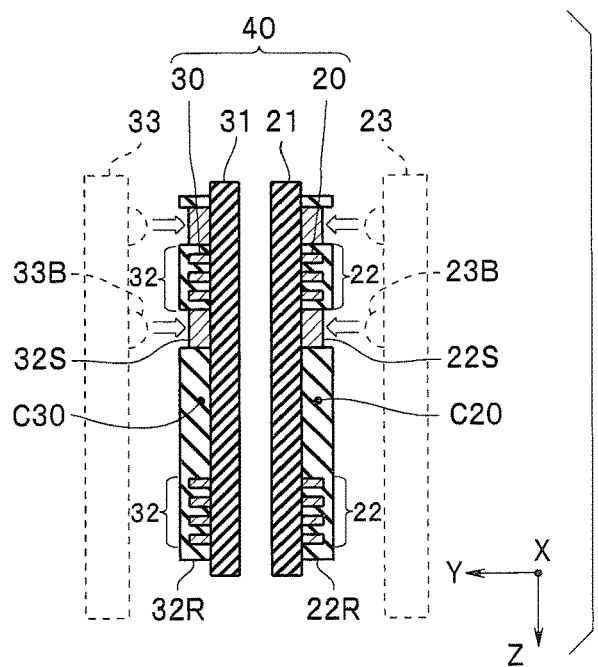
FIG. 4A is an exploded view of the coil assembly of the optical fiber scanning device of the first embodiment.
Figure 4B:
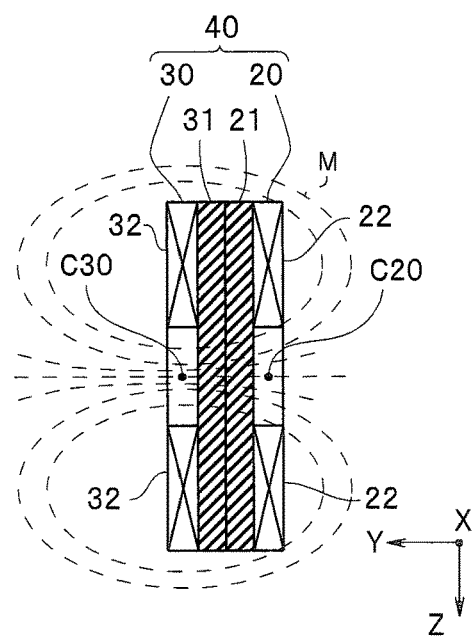
FIG. 4B is a cross-sectional view of the coil assembly of the optical fiber scanning device of the first embodiment.

As shown in FIGS. 3, 4A and 4B, the coil assembly 40 includes a laminated detection coil 20 and drive coil 30. Each of the detection coil 20 and the drive coil 30 is a planar spiral coil formed of a thin film conductor which is wound in a planar shape.

Figure 5:
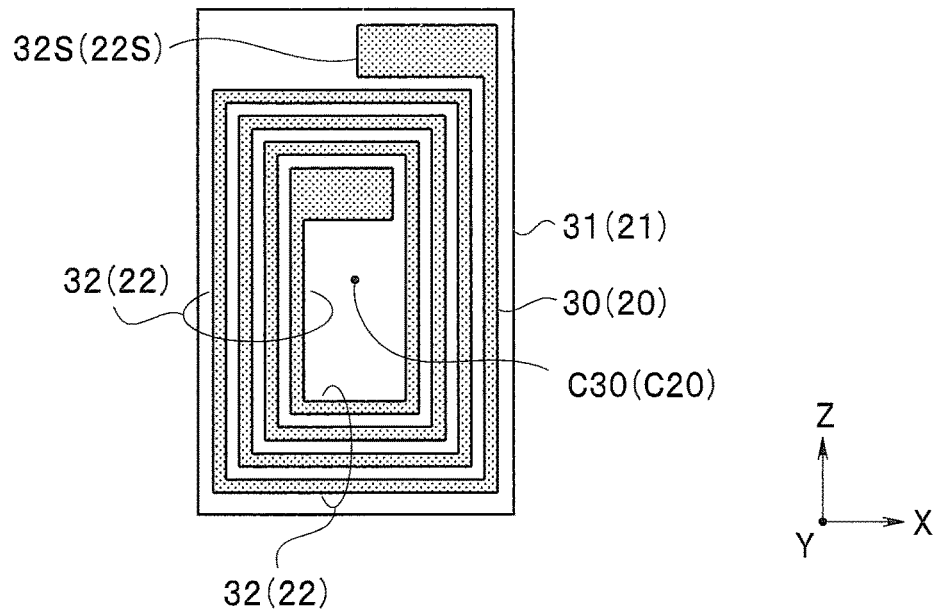
FIG. 5 is a top view of a drive coil (detection coil) of the optical fiber scanning device of the first embodiment.

As shown in FIG. 5, the drive coil 30 disposed on a first coil board 31 includes electrode pads 32S at both end portions of a winding portion 32.

The planar spiral coil is fabricated, for example, by patterning using a resist mask having high accuracy according to an additive method, a subtractive method or the like. The resist mask is fabricated according to a photolithography method using a photoresist and a photomask. In the additive method, for example, a thin film conductor is formed by patterning according to a copper plating method. In the subtractive method, a conductor film is patterned by etching.

For example, the winding portion 32 of the spiral-shaped drive coil 30 which is disposed on the first coil board 31 formed of silicon via an insulating layer (not shown) formed of silicon oxide or the like is covered by an insulating layer 32R formed of resin such as polyimide and epoxy. The insulating layer 32R on the electrode pad 32S includes a contact hole.

Note that in the drive coil 30, the electrode pad 32S is also arranged at a center portion of the winding portion 32. In order to provide the electrode pad 32S around the winding portion 32, the drive coil 30 may further include a single layer of an insulating layer/lead-out wire, or may be a multi-layer coil including plural planar coils laminated via insulating layers as described later.

The electrode pad 32S of the drive coil 30 is bonded to a bump 33B of a first wiring plate 33 by soldering.

As shown in FIG. 4B, when receiving a drive power signal via the first wiring plate 33, the drive coil 30 generates a magnetic field M (see FIG. 4B) in a direction perpendicular to the plane of the coil. The magnetic field M generated by the drive coil 30 which is a spiral coil becomes maximum at a center C30 of the winding portion 32.

The detection coil 20 has a configuration similar to the configuration of the drive coil 30. That is, the detection coil 20 disposed on the second coil board 21 includes electrode pads 22S at both end portions of the detection coil 20. The electrode pad 22S of the detection coil 20 is bonded to a bump 23B of a second wiring plate 23 by soldering.

When the magnetic field varies, the detection coil 20 outputs an induced electromotive force signal according to the variation of the magnetic field. The induced electromotive force signal is transmitted through the second wiring plate 23.

Note that the detection coil 20 may have a configuration different from the configuration of the drive coil 30. That is, the detection coil 20 does not receive large power as in the case of the drive coil 30. Therefore, the detection coil 20 may be, for example, an aluminum thin film pattern which has larger electric resistance than the drive coil 30 formed of a copper plating film, and is disposed, for example, by a sputtering method. It is preferable for enhancement of the detection sensitivity that the winding number (the number of turns) of the detection coil 20 is larger than the winding number of the drive coil 30.

In the optical fiber scanning device 10, the first wiring plate 33, the drive coil 30, the first coil board 31, the second coil board 21, the detection coil 20, and the second wiring plate 23 are laminated in this order to constitute the coil assembly 40.

Note that FIG. 4B shows an example in which the configuration of the coil assembly 40 having the same configuration as the configuration of FIG. 4A is shown in a simplified manner. For example, the winding portion 32 and the like are simplified, and the center C30 of the winding portion 32 is illustrated at the center of the drive coil 30. Note that simplified illustrations are also shown in FIGS. 1 to 3 which have been already used for description.

The drive coil 30 and the detection coil 20 are laminated so that the centers C30 and C20 of the drive coil 30 and the detection coil 20 substantially coincide with each other, and the coil board 31 and the coil board 21 are made to adhere to each other to constitute the coil assembly 40. That is, the drive coil 30 and the detection coil 20 are laminated so as to be superimposed on each other.

In the optical fiber scanning device 10, the coil assembly 40 is arranged so that the drive coil 30 is positioned on the center side (inside) of the housing 11 in order to reduce the intensity of the drive power signal. However, the coil assembly 40 may be arranged so that the detection coil 20 is positioned on the center side of the housing 11.

As already described, when receiving the drive power signal, the drive coil 30 generates a magnetic field M in a direction perpendicular to the plane of the coil. The intensity of the magnetic field M is set by the current value of the drive power signal, the winding number (the number of turns) of the spiral coil, etc. When the direction of the drive power signal flowing in the coil is reversed, the direction of the generated magnetic field is reversed.

As shown in FIG. 2, in the optical fiber scanning device 10, the four coil assemblies 41 to 44 are arranged at rotationally symmetrical positions. That is, the coil assembly 41 and the coil assembly 42 are arranged at positions facing each other, and the coil assembly 43 and the coil assembly 44 are arranged at positions facing each other.

Therefore, the drive coils 30 of the coil assemblies 41 and 42 generate magnetic fields in the Y-axis direction, and the drive coils 30 of the coil assemblies 43 and 44 generate magnetic fields in the X-axis direction.

The optical fiber 13 (magnet 12) is arranged to be equidistant from the four drive coils 30, that is, at the center of a hollow portion of the housing 11.

Next, a method of driving the optical fiber scanning device 10 will be briefly described.

When the drive power signal is supplied to the coil assembly 41 (the drive coil 30), for example, a magnetic field having an N-pole on the inner surface side of the coil assembly 41 is generated. At the same time, when the drive power signal is supplied to the coil assembly 42, for example, a magnetic field having an S-pole on the inner surface side of the coil assembly 42 is generated. That is, the opposing coil assemblies 41 and 42 generate magnetic fields having different magnetic poles on the inner surface sides.

Therefore, for example, an N-pole end on the front side of the magnet 12 arranged in the magnetic field is pulled upwards in the Y-axis direction. Therefore, the free end 13T2 of the optical fiber 13 also moves upwards in the Y-axis direction.

On the other hand, when the drive power signal in the reverse direction is supplied to the coil assemblies 41 and 42, magnetic fields having S-poles on the inner surface sides are generated. Then, the N-pole end of the magnet 12 is pulled downward in the Y-axis direction. Therefore, the free end of the optical fiber 13 also moves downwards in the Y-axis direction.

By controlling the direction of the drive power signal to be supplied to the coil assemblies 41 and 42, that is, supplying the drive power signal which is a current-controlled AC signal, the free end of the optical fiber 13 scans in the Y-axis direction. Likewise, the free end of the optical fiber 13 scans in an X-axis direction orthogonal to the Y-axis direction by controlling the direction of the drive power signal to be supplied to the coil assemblies 43 and 44.

The free end of the optical fiber 13 two-dimensionally scans within the XY plane by controlling the direction of the drive power signal to be supplied to the four coil assemblies 41 to 44. As a result, a light spot emitted from the free end of the optical fiber 13 two-dimensionally scans. The scan width is controlled by the intensity of the drive power signal.

A spiral scanning method, a raster scanning method, or a lissajous method is preferable as the two-dimensional scanning method because image processing is easy, and the raster scanning method is particularly preferable because the raster scanning method can perform uniform illumination.

The magnet 12 and the coil assembly 40 may be arranged so that a driving magnetic field is applied to the rear side of the magnet 12.

Figure 6:
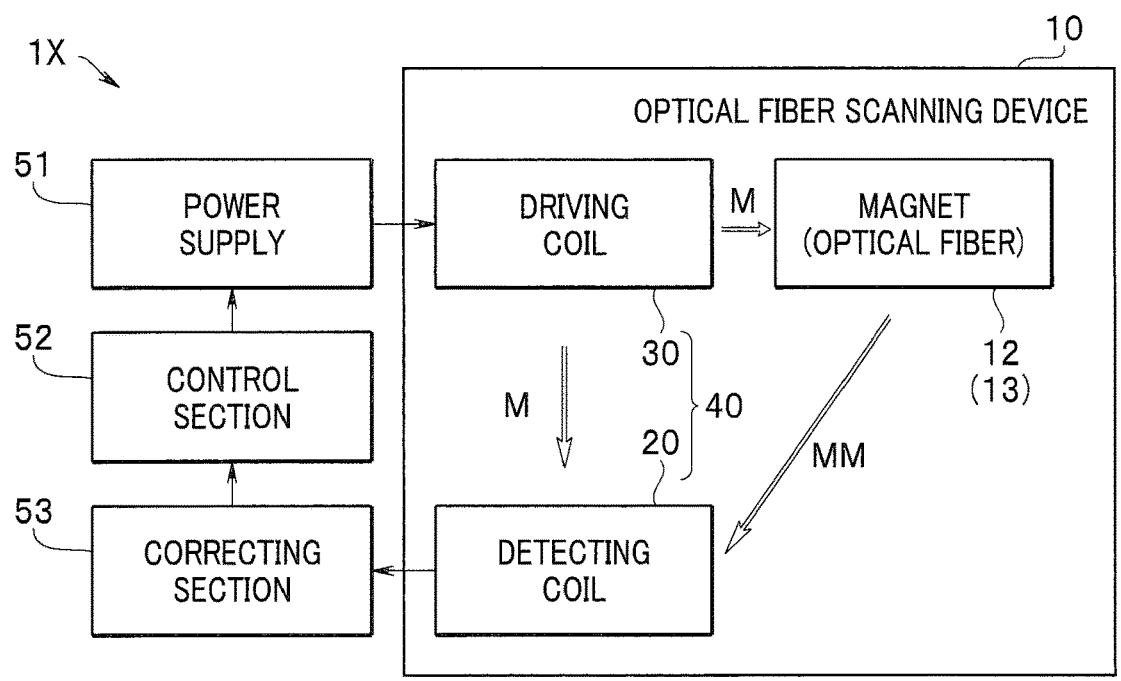
FIG. 6 is a configuration diagram of an optical fiber scanning system including the optical fiber scanning device according to the first embodiment.

As shown in FIG. 6, the optical fiber scanning device 10 constitutes an optical fiber scanning system 1X together with a power supply 51, a control section (controller) 52, and a correcting section (correcting circuit) 53.

The drive power signal outputted from the power supply 51 is supplied to the drive coil 30 via a wire (not shown) and the first wiring plate 33. On the other hand, the induced electromotive force signal outputted from the detection coil 20 is inputted to the correcting section 53 via the second wiring plate 23 and a wire (not shown).

The drive coil 30 generates a magnetic field M when receiving the drive power signal. The magnet 12 is driven (vibrated) by the magnetic field M. When the magnet 12 is driven, the optical fiber 13 on which the magnet 12 is disposed moves (scans).

The detection coil 20 generates an induced electromotive force signal corresponding to variation of a magnetic field. The variation of a magnetic field includes the convolution of variation of a magnetic field MM caused by movement of the magnet 12 disposed on the optical fiber 13 and variation of a magnetic field M generated by the drive coil 30.

The correcting section 53 cancels the influence of the induced electromotive force caused by the magnetic field M generated by the drive coil 30 from the induced electromotive force signal outputted from the detection coil 20, and outputs a correction signal which is an induced electromotive force signal based on the movement of the magnet 12. The control section 52 controls the drive power signal outputted from the power supply 51 based on the output (correction signal) of the correcting section 53.

For example, in the correcting section 53 including CPU, the output is adjusted so as to cancel the induced electromotive force signal outputted by the detection coil 20 under a state where the magnet 12 has no influence, a state where a drive power signal having a frequency at which the optical fiber 13 is not driven is supplied to the drive coil 30. When a frequency at which the optical fiber is driven and a frequency at which this adjustment value is set are close to each other, it is little necessary to change this adjustment value even when a drive frequency changes.

For example, the control section 52 including CPU obtains information on a movement state of the magnet 12, that is, a movement state (driving state) of the free end 13T2 of the optical fiber 13, for example, amplitude, phase, etc. on a real-time basis from the induced electromotive force signal (correction signal) based on only the variation of the magnetic field MM caused by the movement of the magnet 12 disposed on the optical fiber 13. The control section 52 controls the drive power signal outputted from the power supply 51 so that the optical fiber 13 is set to a predetermined drive state set in advance.

For example, when the amplitude of the movement (scanning) of the magnet 12 is smaller than a predetermined value, the control section 52 controls the power supply 51 so as to increase the absolute value of the drive power signal. Therefore, the optical fiber scanning device 10 can perform efficient and stable scanning irradiation.

Note that the drive coil of the coil assembly 41 and the drive coil of the coil assembly 42 which are arranged to face each other are connected in series to each other. Likewise, the drive coil of the coil assembly 43 and the drive coil of the coil assembly 44 which are arranged to face each other are connected in series to each other. Furthermore, the detection coil of the coil assembly 41 and the detection coil of the coil assembly 42 which are arranged to face each other are connected in series to each other, and the detection coil of the coil assembly 43 and the detection coil of the coil assembly 44 which are arranged to face each other are connected in series to each other.

For example, each of the detection coil 20 and the drive coil 30 shown in FIG. 6 represents two coils connected in series. That is, the optical fiber scanning system 10X including the four coil assemblies 41 to 44 includes two correcting sections 53, two control sections 52, and two power supplies 51.

In the optical fiber scanning device 10 in which the detection coil 20 and the drive coil 30 are planar spiral coils, two detection coils 20 having the same configuration can be arranged in opposite positions. A detection signal outputted from the two detection coils 20 connected in series, that is, an induced electromotive force signal is twice as large as a detection signal outputted from one detection coil 20. Furthermore, the detection signal outputted from one detection coil 20 increases or decreases according to the distance between the magnet 12 and the detection coil 20 even at the same moving speed of the magnet 12. On the other hand, the detection signal outputted from the two detection coils 20 which are arranged to face each other and connected in series to each other are substantially proportional to the moving speed of the magnet 12 because the detection signals of the detection coils 20 are added to each other. Therefore, it is easy to perform the control by the control section 52. Note that a method of measuring the relationship between the amplitude of the optical fiber and the detection signal in advance and performing feedback on the drive power signal by using the measurement or the like is available in order to perform more accurate control.

Needless to say, the four coil assemblies 41 to 44 may be controlled by the respective control sections 52 or the like. Conversely, one control section 52 may perform drive control in the X and Y directions, that is, control the four coil assemblies 41 to 44. In addition, the correcting section 53 and the control section 52 may be constituted by one CPU.

In the optical fiber scanning device 10, the drive coil 30 and the detection coil 20 are planar spiral coils. Therefore, the optical fiber scanning device 10 is smaller in diameter than a conventional optical fiber scanning device having a bulk magnetic body and a bulk conductor. Furthermore, in the optical fiber scanning device 10, the coil assemblies 40 each including the laminated drive coil 30 and detection coil 20 can be arranged at the positions facing each other. Since the optical fiber scanning device 10 can apply a magnetic field to the magnet 12 from the drive coils located on both sides of the magnet 12, the optical fiber scanning device 10 has a higher driving efficiency than the conventional optical fiber scanning device in which a drive coil can be arranged only on one side of a magnet.

Modification

Next, optical fiber scanning devices according to modifications of the first embodiment will be described. Since the optical fiber scanning devices according to the modifications are similar to the optical fiber scanning device 10 and have the same effect, the components having the same functions are represented by same reference signs, and description of these components will be omitted.

Modification 1

Figure 7A:
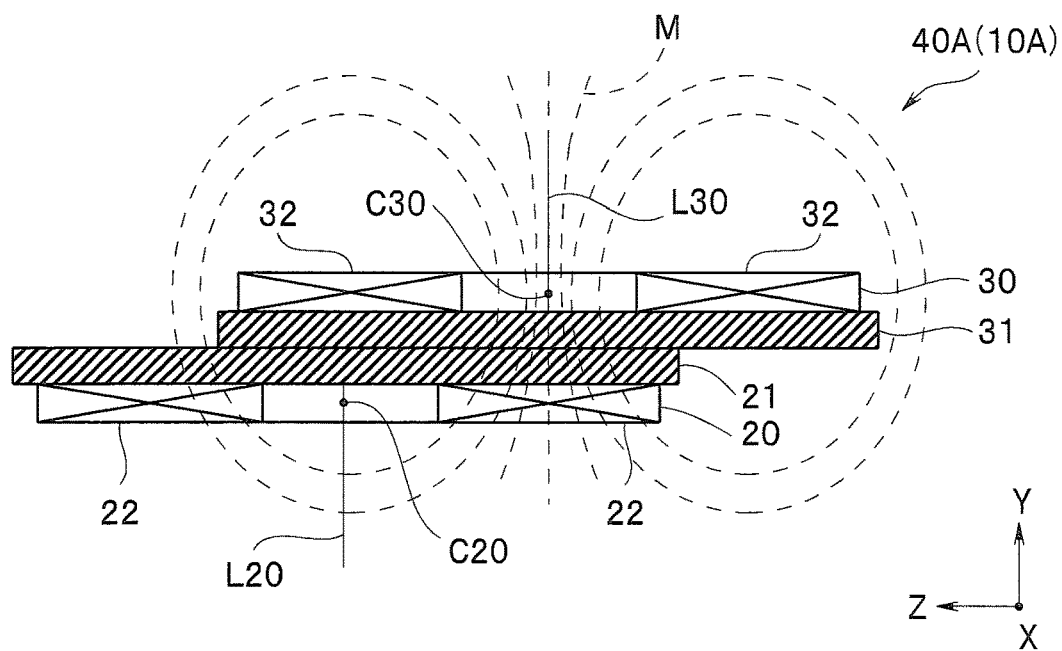
FIG. 7A is a cross-sectional view of a coil assembly of an optical fiber scanning device according to a modification 1 of the first embodiment.
Figure 7B:
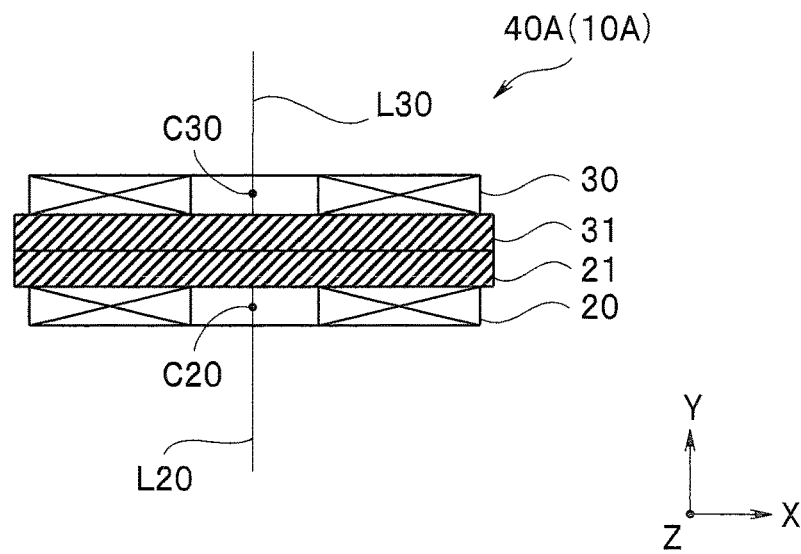
FIG. 7B is a cross-sectional view of the coil assembly of the optical fiber scanning device according to the modification 1 of the first embodiment.

As shown in FIGS. 7A and 7B, a coil assembly 40A of an optical fiber scanning device 10A according to modification 1 is arranged so that the center C20 of the winding portion 22 of the detection coil 20 is eccentric from the center C30 of the winding portion 32 of the drive coil 30 and overlaps the winding portion 32 in plan view. In other words, a center line L30 which passes through the center C30 of the drive coil 30 and is orthogonal to the coil plane does not coincide with a center line L20 which passes through the center C20 of the detection coil 20 and is orthogonal to the coil plane. A central region inside the winding portion 22 of the detection coil 20 overlaps the winding portion 32 of the drive coil 30.

That is, a cross-sectional view (FIG. 7B) of the coil assembly 40A orthogonal to the optical axis is substantially identical to a cross-sectional view (for example, FIG. 4B) of the optical fiber scanning device 10 of the first embodiment. However, in a cross-section view parallel to the optical axis (FIG. 7A), the center C30 of the drive coil 30 and the center C20 of the detection coil 20 do not overlap each other.

As compared with the optical fiber scanning device 10, in the optical fiber scanning device 10A, the drive coil 30 shifts rearward in parallel to the optical axis direction with respect to the detection coil 20. Conversely, in the coil assembly 40A, the detection coil 20 may shift rearward in parallel in the optical axis direction with respect to the drive coil 30.

As described above, the magnetic field M generated by the drive coil 30 is maximum at the center C30 of the drive coil 30. Then, the magnetic field M becomes extremely small just above and just below the winding portion 32 of the drive coil 30. This is because magnetic fields generated by adjacent conductors of the winding portion 32 cancel each other.

The detection coil 20 outputs an induced electromotive force signal corresponding to variation of a magnetic field penetrating through the central region inside the winding portion 22.

Therefore, the coil assembly 40A which is arranged so that the center C20 of the detection coil 20 overlaps the winding portion 32 of the drive coil 30 has a little signal component (noise component) which is contained in the induced electromotive force signal and caused by the variation of the magnetic field M generated by the drive coil 30, so that a signal component generated by the variation of the magnetic field MM following the movement of the magnet 12 can be acquired with a higher S/N (signal/noise) ratio.

The relative positional relationship between the detection coil 20 and the drive coil 30 described above can be realized because the detection coil 20 and the drive coil 30 are planar spiral coils.

Modification 2

As in the case of the coil assembly 40A, a coil assembly 40B of an optical fiber scanning device 10B according to a modification 2 is arranged so that the center C20 of the detection coil 20 is eccentric from the center C30 of the drive coil 30 and overlaps the winding portion 32 of the drive coil 30 in plan view.

Figure 8A:
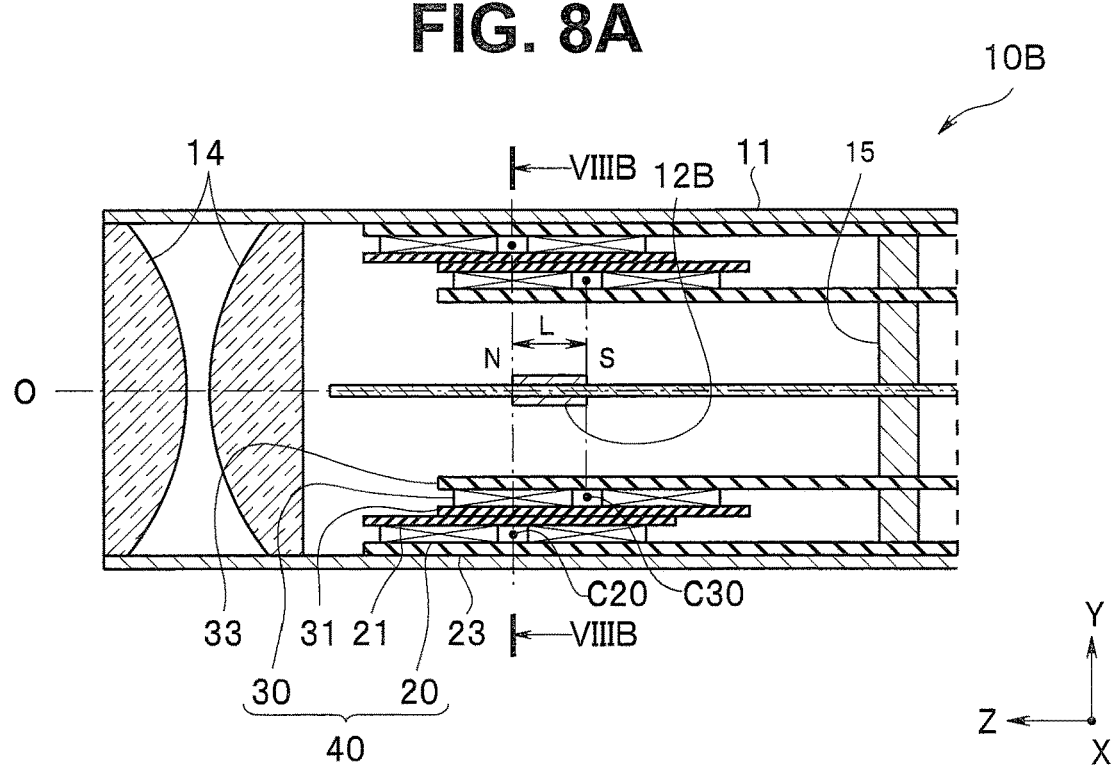
FIG. 8A is a cross-sectional view of the coil assembly of an optical fiber scanning device according to a modification 2 of the first embodiment.
Figure 8B:
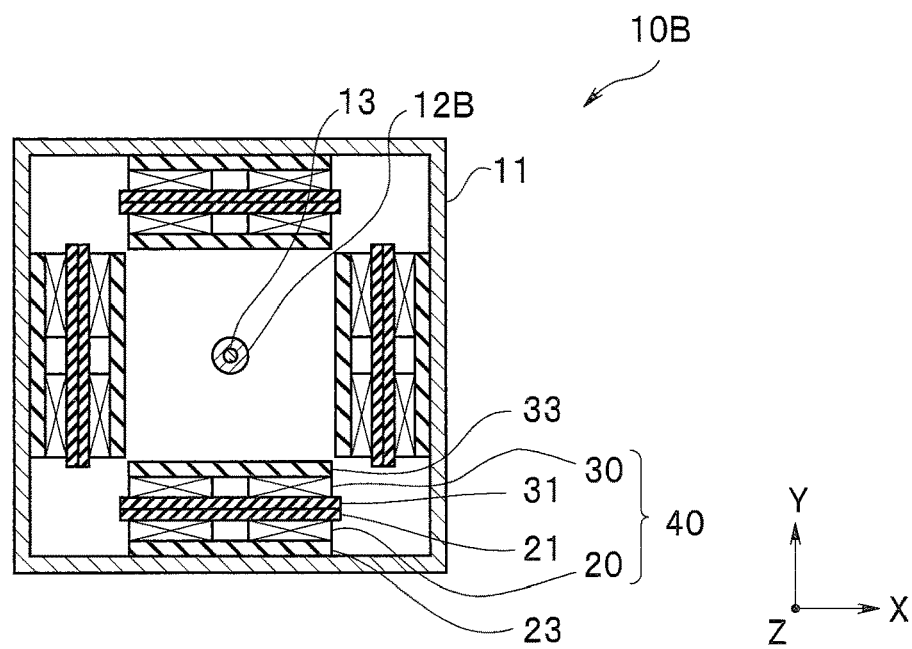
FIG. 8B is a cross-sectional view of the coil assembly of the optical fiber scanning device according to the modification 2 of the first embodiment.

As shown in FIGS. 8A and 8B, in the optical fiber scanning device 10B, one end portion (for example, S-pole side) of the magnet 12B is arranged on a line connecting the centers C30 of the drive coils 30 which are arranged so as to face each other, and the other end portion (for example, N-pole side) of the magnet 12B is arranged on a line connecting the centers C20 of the detection coils 20 which are arranged so as to face each other.

In other words, the length L of the magnet 12B is substantially equal to the distance between the center C20 of the detection coil 20 and the center C30 of the drive coil 30.

In the optical fiber scanning device 10B, the magnetic field M generated by the drive coil 30 is most strongly applied to a rear end portion of the magnet 12B. On the other hand, the magnetic field MM generated by a distal end portion of the magnet 12B is efficiently applied to the detection coil 20.

That is, in the optical fiber scanning device 10B, a driving magnetic field M generated by the drive coil 30 is applied to one end portion (for example, S-pole side) of the magnet 12B magnetized in a longitudinal axis direction, and the magnetic field MM generated by the other end portion (for example, N-pole side) of the magnet 12B is detected by the detection coil 20.

The optical fiber scanning device 10B has the effect of the optical fiber scanning device 10A, and further is excellent in the efficiency of applying the magnetic field M to the magnet 12B by the drive coil 30 and the detection efficiency (S/N ratio) of the magnetic field MM from the magnet 12B by the detection coil 20.

The distance between the center C20 of the detection coil 20 and the center C30 of the drive coil 30 is not necessarily required to be perfectly equal to the length L of the magnet 12B, and it is possible to perform highly efficient application and detection of a magnetic field, for example, in the case where the distance ranges from not less than 0.50 L to not more than 1.50 L. In other words, it is not necessary that the position of the end portion of the magnet 12B is strictly located on the line connecting the centers of the coils.

Modification 3

Figure 9A:
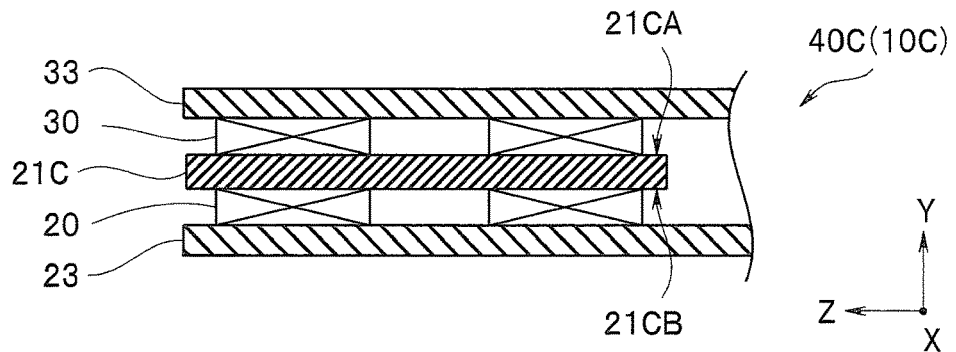
FIG. 9A is a cross-sectional view of the coil assembly of an optical fiber scanning device according to a modification 3 of the first embodiment.
Figure 9B:
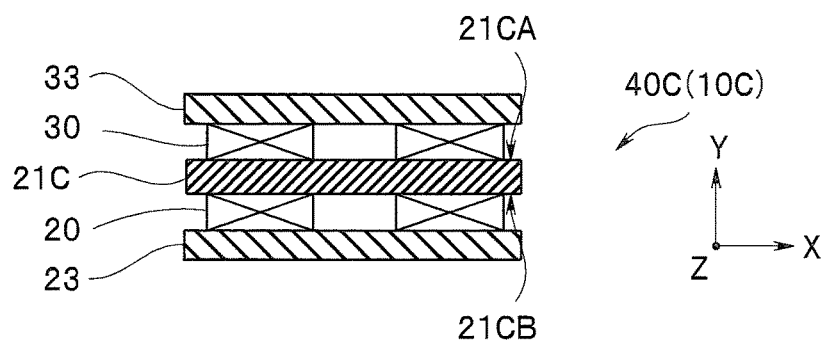
FIG. 9B is a cross-sectional view of the coil assembly of the optical fiber scanning device according to the modification 3 of the first embodiment.

As shown in FIGS. 9A and 9B, in a coil assembly 40C of an optical fiber scanning device 10C according to a modification 3, the drive coil 30 and the detection coil 20 are disposed on one coil board 21C. The drive coil 30 is disposed on a first principal surface 21CA of the coil board 21C, and the detection coil 20 is disposed on a second principal surface 21CB facing the first principal surface 21CA.

For example, plural coil assemblies 40C can be fabricated by fragmenting, into individual pieces, a silicon wafer in which plural drive coils 30 are disposed on the first principal surface 21CA and plural detection coils 20 are arranged on the second principal surface 21CB facing the first principal surface 21CA.

The coil assembly 40C of the optical fiber scanning device 10C can be easily manufactured because the drive coil 30 and the detection coil 20 are not required to be laminated while positioned. The optical fiber scanning device 10C has a smaller diameter because the thickness of the coil assembly 40C is smaller than the thickness of the coil assembly 40.

Modification 4

Figure 10A:
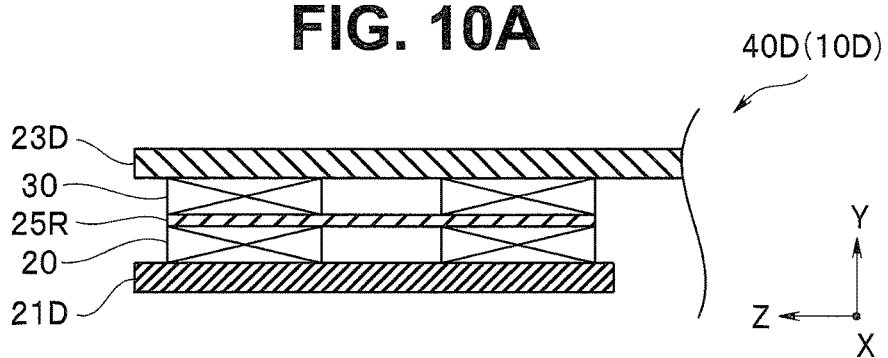
FIG. 10A is a cross-sectional view of a coil assembly of an optical fiber scanning device according to a modification 4 of the first embodiment.
Figure 10B:
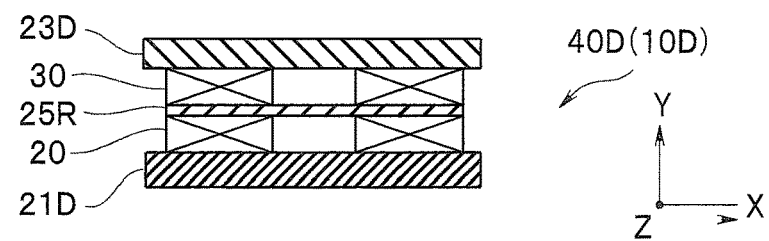
FIG. 10B is a cross-sectional view of the coil assembly of the optical fiber scanning device according to the modification 4 of the first embodiment.

As shown in FIGS. 10A and 10B, a coil assembly 40D of an optical fiber scanning device 10D according to a modification 4 is a multi-layer coil in which a drive coil 30 and a detection coil 20 disposed on a coil board 21D are provided on the same principal surface 21DA of one coil board 21D via an insulating layer 25R.

The drive coil 30 and the detection coil 20 of the coil assembly 40D are connected to the same wiring plate 23D. The coil assembly 40D of the optical fiber scanning device 10D receives a drive power signal via a wiring plate 23D and transmits an induced electromotive force signal.

Plural coil assemblies 40D can be fabricated, for example, by arranging plural drive coils 30 and plural detection coils 20 on one surface of a silicon wafer via insulating layers 25R in a multilayer configuration and fragmenting the resultant multilayer into individual pieces.

The optical fiber scanning device 10D has the effect of the optical fiber scanning device 10C and further has a smaller diameter because only one wiring plate is provided.

In order to more reduce the diameter in the optical fiber scanning device 10D, for example, the coil board 21D may be processed to be thinner by polishing processing, or the coil board 21D may be perfectly removed by etching processing which leaves only a silicon oxide layer which is an insulating layer formed on the surface of the coil board 21D.

Modification 5

Figure 11A:
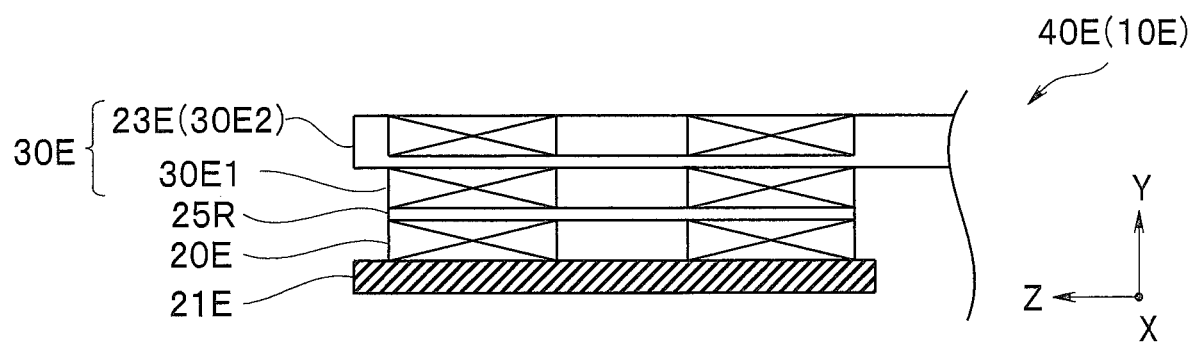
FIG. 11A is a cross-sectional view of a coil assembly of an optical fiber scanning device according to a modification 5 of the first embodiment.
Figure 11B:
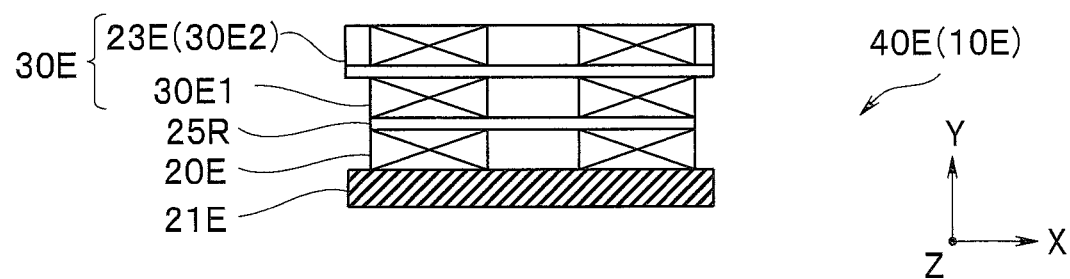
FIG. 11B is a cross-sectional view of the coil assembly of the optical fiber scanning device according to the modification 5 of the first embodiment.
Figure 11C:
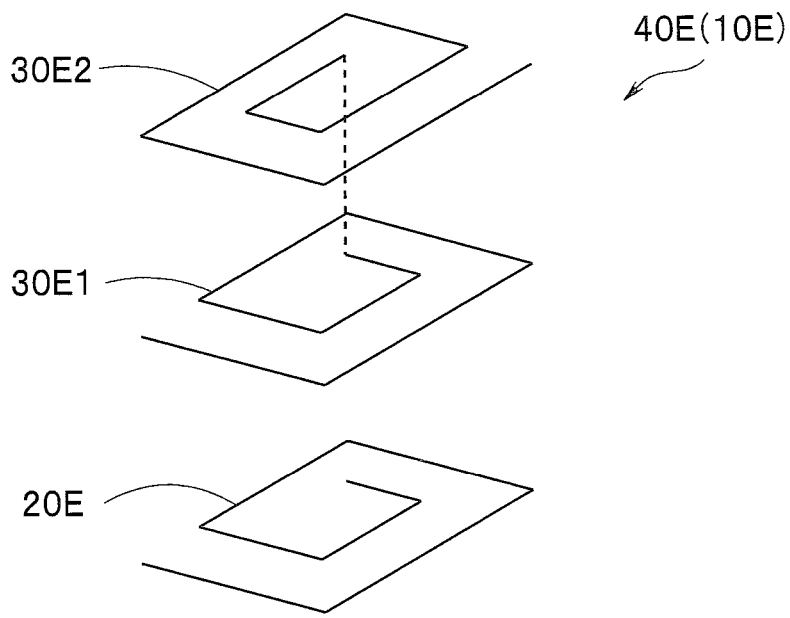
FIG. 11C is a schematic diagram of the coil assembly of the optical fiber scanning device according to the modification 5 of the first embodiment.

As shown in FIGS. 11A, 11B, and 11C, in a coil assembly 40E of an optical fiber scanning device 10E according to a modification 5, a part 30E2 of a drive coil 30E is constituted by a multilayer wiring plate 23E configured to transmit a drive power signal and an induced electromotive force signal.

A multilayer wiring plate 23E on which a drive coil 30E2 is configured is joined to a multilayer coil including a detection coil 20E disposed on the coil board 21E and a drive coil 30E1 disposed via an insulating layer 25R. End portions of the drive coil 30E1 and the drive coil 30E2 are connected to each other to constitute a two-layer coil.

The optical fiber scanning device 10E has small drive power because the drive coil 30 is the two-layer coil, and also can be easily manufactured because the drive coil 30E2 is constituted by the multilayer wiring plate 23E.

The detection coil arranged inside the housing 11 may be the two-layer coil constituted by the first detection coil on the coil board and the second detection coil on the multilayer wiring plate. For example, the detection coil may be a two-layer coil on the coil board, and the drive coil may be constituted by a multilayer wiring plate.

An optical fiber scanning device in which at least a part of a drive coil or a detection coil is constituted by a multilayer wiring plate has an effect similar to the effect of the optical fiber scanning device 10E.

Modification 6

Figure 12A:
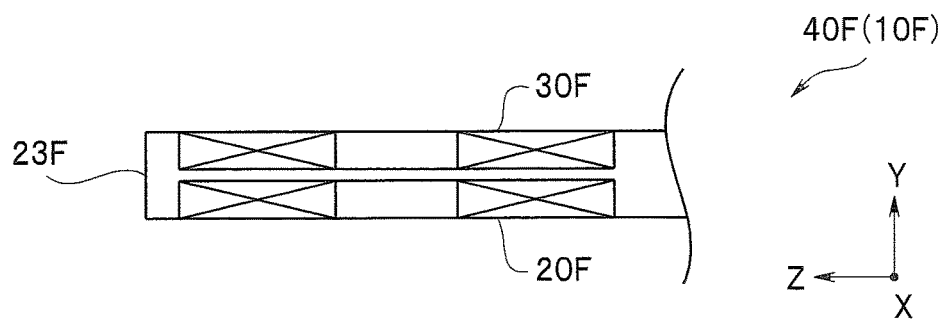
FIG. 12A is a cross-sectional view of a coil assembly of an optical fiber scanning device according to a modification 6 of the first embodiment.
Figure 12B:
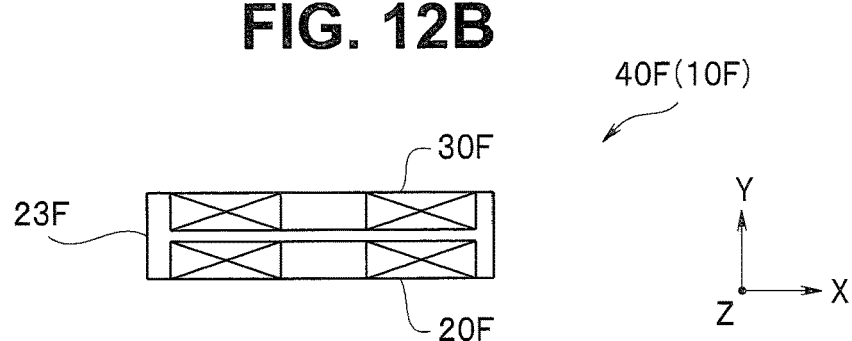
FIG. 12B is a cross-sectional view of the coil assembly of the optical fiber scanning device according to the modification 6 of the first embodiment.

As shown in FIGS. 12A and 12B, in a coil assembly 40F of an optical fiber scanning device 10F according a modification 6, a drive coil 30F and a detection coil are constituted by a multilayer wiring plate 23F. The coil assembly 40F contains no coil board.

At least any one of the drive coil 30F and the detection coil may be a multilayer coil of two or more layers.

The optical fiber scanning device 10F can be easily manufactured because the coil assembly 40F is constituted by the multilayer wiring plate 23F, and also has a small diameter because the optical fiber scanning device 10F contains no coil board. When a flexible board is used as the multilayer wiring plate 23F, the degree of freedom of the shape of the optical fiber scanning device 10F is enhanced because the multilayer wiring plate can be bent, for example, so as to be wound around the optical axis.

Modification 7

Figure 13:
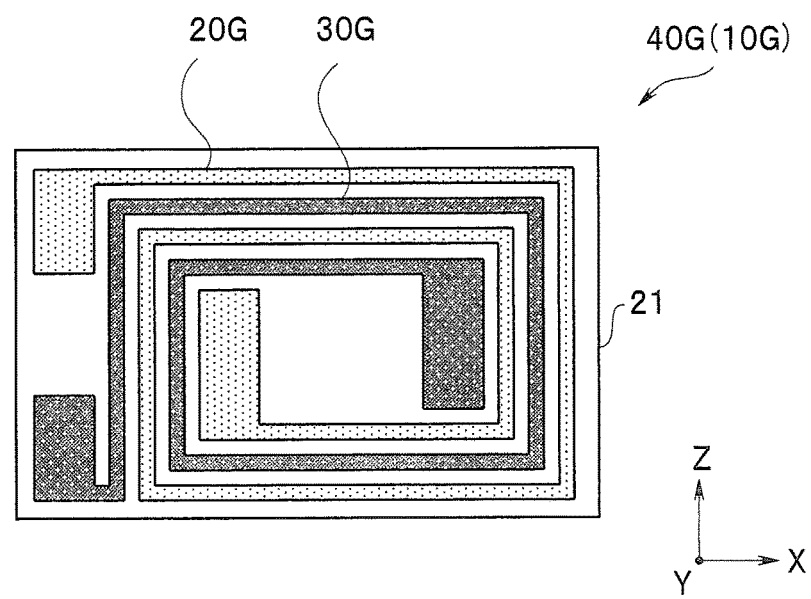
FIG. 13 is a top view of a coil assembly of an optical fiber scanning device according to a modification 7 of the first embodiment.

As shown in FIG. 13, in a coil assembly 40G of an optical fiber scanning device 10G according to a modification 7, a drive coil 30G and a detection coil 20G are disposed on the same principal surface of a coil board 21. The drive coil 30G and the detection coil 20G constitute a composite coil in which the centers of the windings of the drive coil 30G and the detection coil 20G are substantially coincident with each other.

The coil assembly 40G of the optical fiber scanning device 10G can be easily manufactured because the drive coil and the detection coil are not required to be positioned and laminated. The optical fiber scanning device 10G has a small diameter because the thickness of the coil assembly 40G is small.

Modification 8

Figure 14:
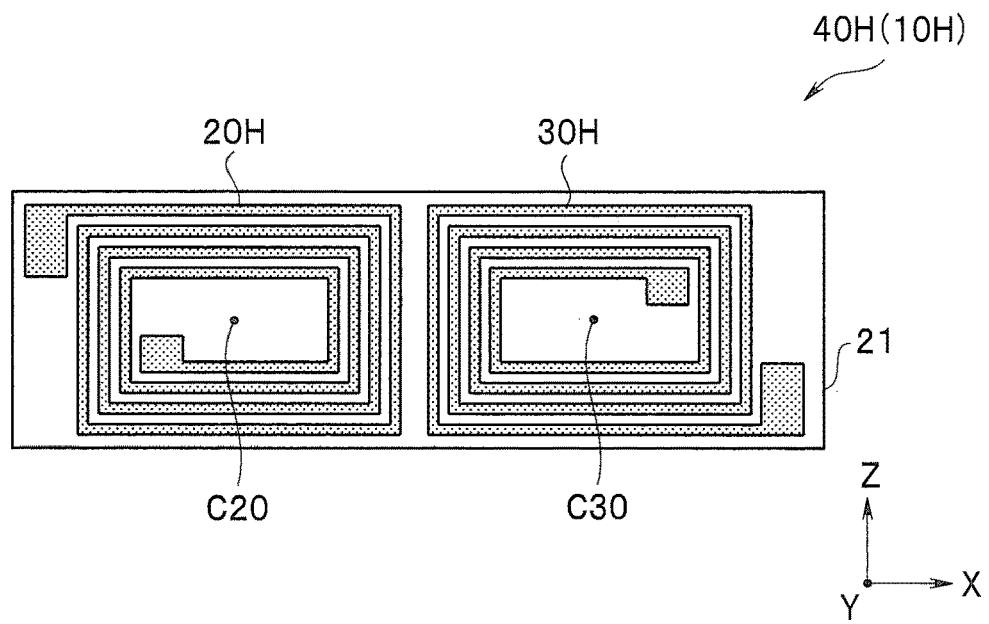
FIG. 14 is a top view of a coil assembly of an optical fiber scanning device according to a modification 8 of the first embodiment.

As shown in FIG. 14, in a coil assembly 40H of an optical fiber scanning device 10H according to a modification 8, a drive coil 30H and a detection coil 20H are disposed on the same principal surface of the coil board 21. The drive coil 30H and the detection coil 20H are disposed at different places.

The coil assembly 40H of the optical fiber scanning device 10H is easily manufactured because it is unnecessary to position and laminate the drive coil and the detection coil. The optical fiber scanning device 10H has a small diameter because the thickness of the coil assembly 40H is small.

Although not shown, when the length of the magnet is substantially equal to the distance between the center C20 of the detection coil 20H and the center C30 of the drive coil 30H, the optical fiber scanning device 10H has also the same effect as the optical fiber scanning device 10B which has already been described.

Modification 9

Figure 15:
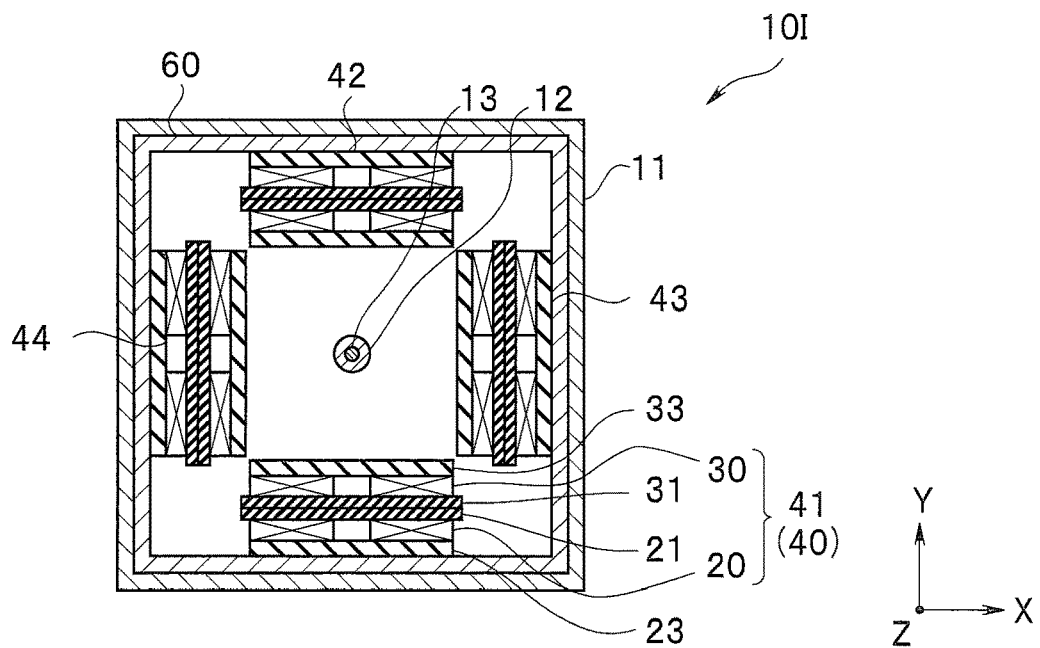
FIG. 15 is a cross-sectional view of an optical fiber scanning device according to a modification 9 of the first embodiment.

As shown in FIG. 15, in an optical fiber scanning device 10I according to a modification 9, a yoke 60 formed of soft magnetic body is arranged on an outer surface side of the drive coil 30 and the detection coil 20.

The yoke 60 is a magnetic field inducing section configured to induce a magnetic field generated by the drive coil 30. It is preferable that the yoke 60 is formed of a soft magnetic material having a relative magnetic permeability of 100 or more at the frequency of the drive power signal, for example, iron, cobalt, nickel, permalloy, soft ferrite or amorphous alloy.

The optical fiber scanning device 10I can drive the drive coil 30 with lower power because not only the magnetic field M generated by the drive coil 30 hardly leaks to the outside, but also the efficiency of applying the magnetic field M to the magnet 12 is high.

Needless to say, the housing 11 is formed of soft magnetic body and used as a yoke.

Modification 10 and 11

The optical fiber scanning devices 10, 10A to 10I include the four coil assemblies 41 to 44, drive the optical fiber 13 by using the coil assemblies 41 to 44, and detect the driving state by the respective detection coils 20 of the coil assemblies 41 to 44.

For example, even when only the two orthogonally arranged coil assemblies 41 and 43 are driven, two-dimensional scanning is possible. Furthermore, in the case of an optical fiber scanning device requiring only one-dimensional scanning, the scanning can be performed with only one coil assembly 41.

Figure 16:
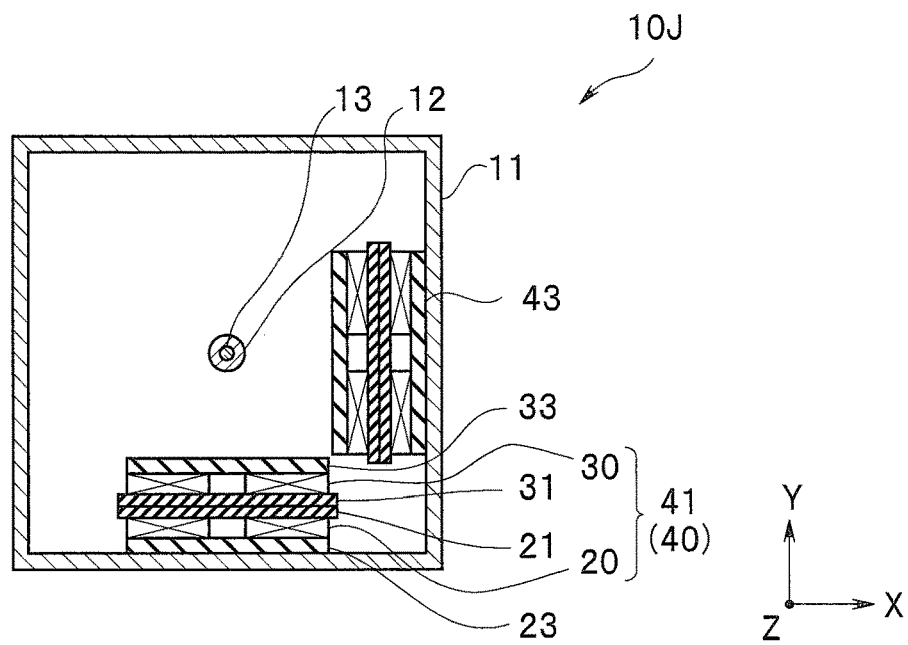
FIG. 16 is a cross-sectional view of an optical fiber scanning device according to a modification 10 of the first embodiment.
Figure 17:
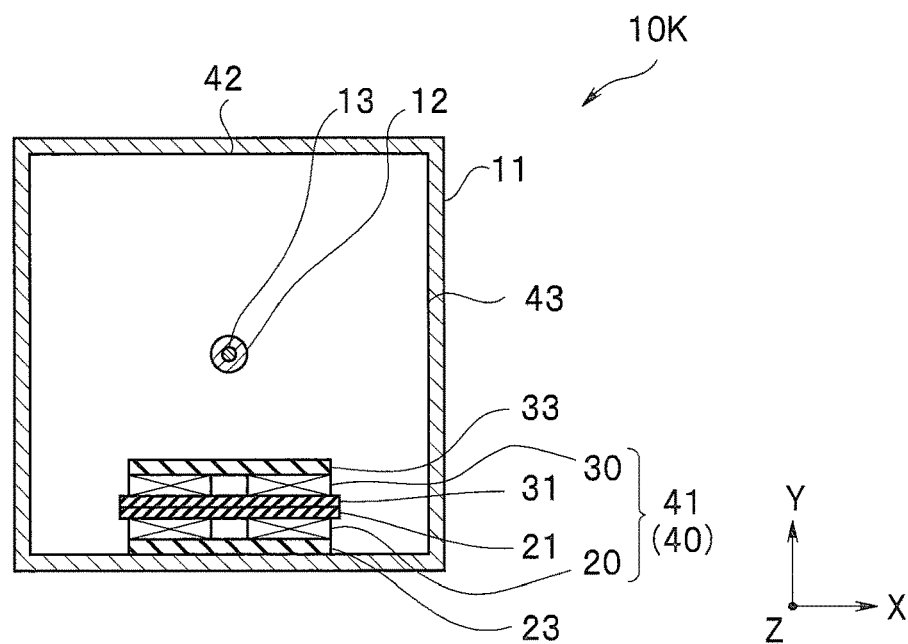
FIG. 17 is a cross-sectional view of an optical fiber scanning device according to a modification 11 of the first embodiment.

Since an optical fiber scanning device 10J according to a modification 10 shown in FIG. 16 includes two coil assemblies 41 and 43 arranged orthogonally, the optical fiber scanning device 10J can perform two-dimensional scanning. Since an optical fiber scanning device 10K according to a modification 11 shown in FIG. 17 includes one coil assembly 41, the optical fiber scanning device 10K can perform one-dimensional scanning.

The optical fiber scanning devices 10C to 10K would also have the same effect as the optical fiber scanning device 10A when the center of the detection coil is eccentric from the center of the drive coil and arranged so as to overlap the winding of the drive coil in plan view of the coil assembly.

The optical fiber scanning devices 10C to 10K would also have the same effect as the optical fiber scanning device 10B when one end portion of the magnet is arranged on a line connecting the centers of the detection coils which are arranged so as to face each other, and the other end portion of the magnet is arranged on a line connecting the centers of the drive coils which are arranged so as to face each other.

Second Embodiment

Next, endoscope systems 1, 1A to 1J including optical scanning type endoscopes (endoscopes) 2, 2A to 2J of a second embodiment will be described.

Figure 18:
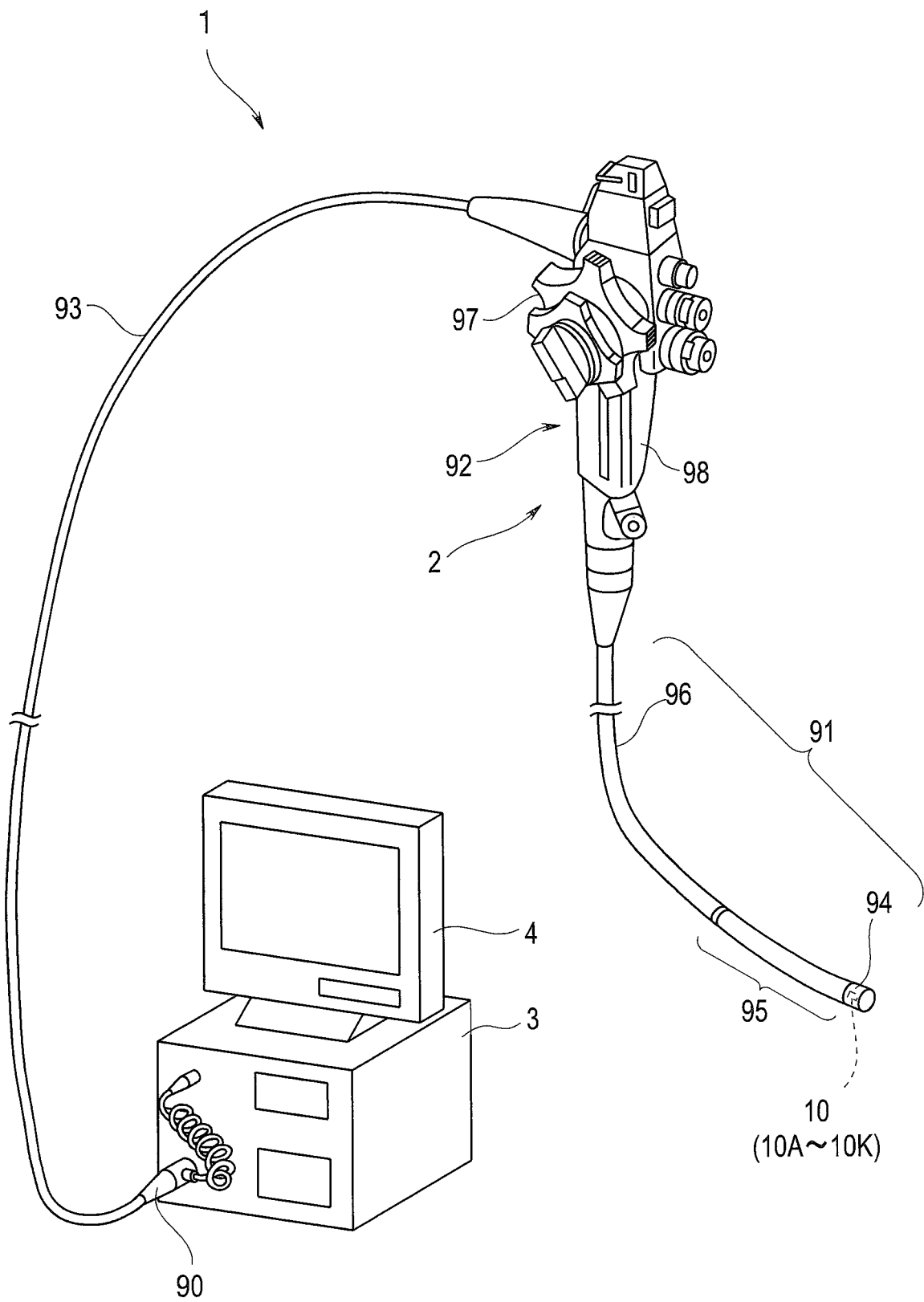
FIG. 18 is a perspective view of an endoscope system including an optical scanning type endoscope according to a second embodiment.

An endoscope 2 of the present embodiment shown in FIG. 18 is an optical scanning type endoscope in which any of the optical fiber scanning devices 10, 10A to 10K described above is equipped to a rigid distal end portion 94 of an insertion section 91. The endoscope 2 having the optical fiber scanning device 10 will be described as an example.

An endoscope system 1 including the endoscope 2 includes the endoscope 2, a main body 3, and a monitor 4. The endoscope 2 irradiates a subject with illumination light while scanning the illumination light two-dimensionally by the optical fiber scanning device 10, detects reflected light (return light) from the subject, performs data processing in the main body 3, and displays a generated subject image on the monitor 4.

The endoscope 2 includes an elongated insertion section 91 inserted into a living body, an operation section 92, and a universal cable 93 in which an electric cable and the like are inserted. The insertion section 91 of the endoscope 2 includes a rigid distal end portion 94, a bending portion 95, and a flexible tube portion 96. The endoscope 2 of the embodiment is a so-called flexible endoscope, but has an effect described later even when the insertion section 91 is a hard, so-called rigid endoscope.

A bending operation knob 97 configured to perform a bending operation on the bending portion 95 is disposed on the operation section 92. A connecting portion between the insertion section 91 and the operation section 92 is a grasping portion 98 to be gripped by a user.

The universal cable 93 extending from the operation section 92 is connected to the main body 3 via a connector 90. The main body 3 is connected to the monitor 4 configured to display an endoscope image.

Figure 19:
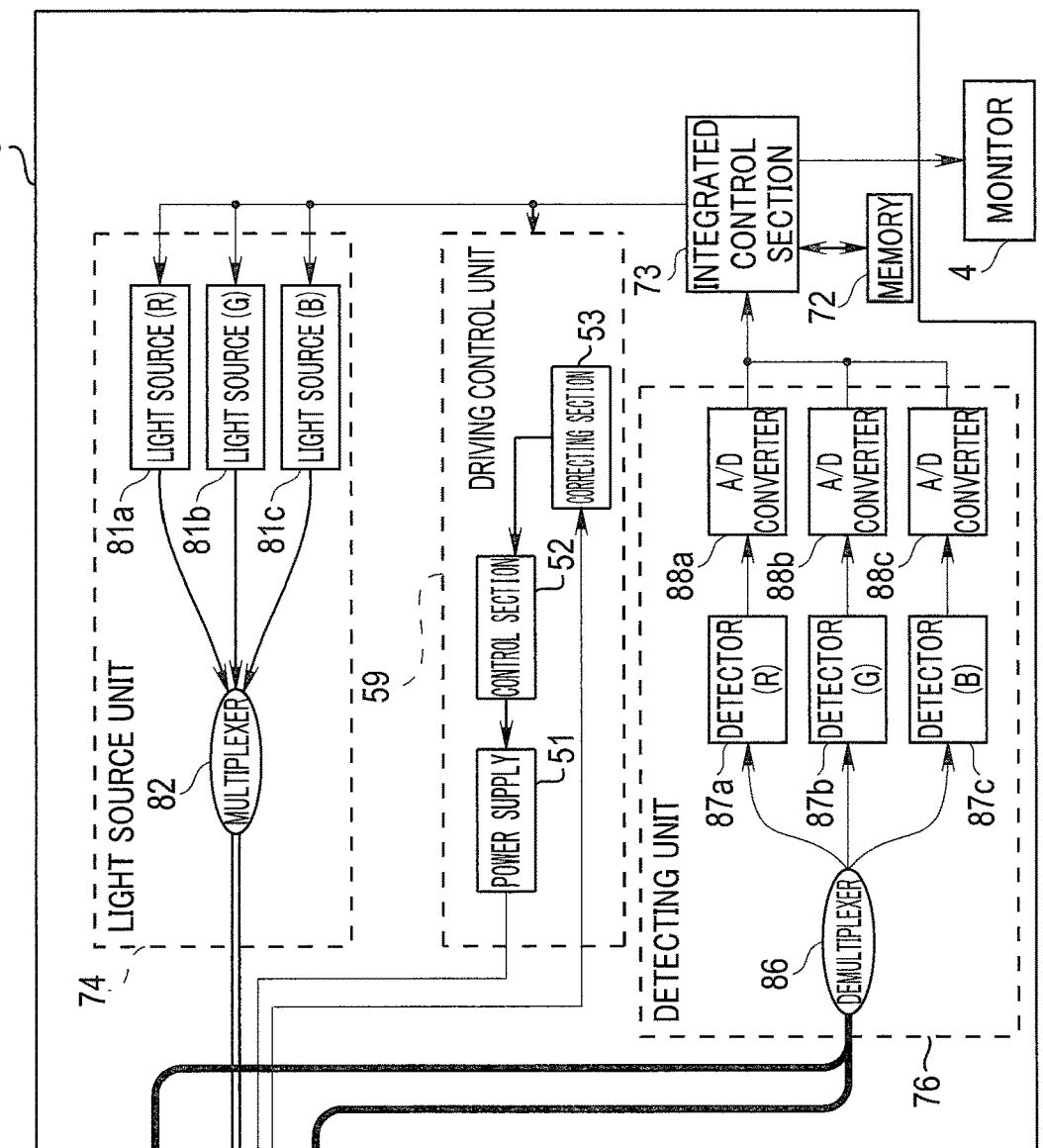
FIG. 19 is a configuration diagram of the endoscope system including the optical scanning type endoscope according to the second embodiment.

Next, the configuration of the endoscope system 1 is shown in FIG. 19.

A detection fiber 27 which is inserted from a proximal end side to a distal end side along the inner circumference of the insertion section 91 and guides reflected light from the subject is provided inside the insertion section 91 of the endoscope 2. A detection optical system 27A is disposed at the distal end of the detection fiber 27. When the connector 90 of the endoscope 2 is connected to the main body 3, the detection fiber 27 is connected to a demultiplexer 86.

The main body 3 includes a drive control unit 59, a memory 72, an integrated control section (integrated controller) 73, a light source unit 74, and a detection unit 76. The light source unit 74 has three light sources 81a, 81b, 81c and a multiplexer 82.

As described with reference to FIG. 6, the drive control unit 59 includes a correcting section 53 to which an induced electromotive force signal outputted from the detection coil 20 is inputted, a power supply 51 configured to output a drive power signal to the drive coil 30, and a control section 52 configured to control the power supply 51 based on a correction signal outputted by the correcting section 53.

A control program, etc. to control the overall main body 3 are stored in the memory 72.

The integrated control section 73 reads out a control program from the memory 72, and controls the light source unit 74 and the drive control unit 59. The integrated control section 73 performs control to execute data processing on a light intensity signal of the reflected light from the subject detected by the detection unit 76 and display an image on the monitor 4.

The light sources 81a, 81b, and 81c of the light source unit 74 respectively emit light in different wavelength bands, for example, light of a wavelength band of R (red), light of a wavelength band of G (green), and light of a wavelength band of B (blue) to the multiplexer 82 under the control of the integrated control section 73. The multiplexer 82 multiplexes the lights in the wavelength bands of R, G, and B, and outputs the multiplexed light to the optical fiber 13.

Under the control of the integrated control section 73, the drive control unit 59 outputs, to the drive coil 30, a drive power signal with which the distal end of the optical fiber 13 of the optical fiber scanning device 10 scans in a desired scanning manner That is, the drive control unit 59 outputs a preset drive power signal to the coil assemblies 40 of the optical fiber scanning device 10 so as to drive the distal end of the optical fiber 13 in the right-and-left direction (X-axis direction) and the up-and-down direction (Y-axis direction) with respect to the insertion axis (Z-axis) of the insertion section 91.

The detection fiber 27 receives reflected light reflected from the surface of the subject and guides the received reflected light to the demultiplexer 86. The demultiplexer 86 is, for example, a dichroic mirror or the like, and demultiplexes the reflected light for each predetermined wavelength band. Specifically, the demultiplexer 86 demultiplexes the reflected light guided by the detection fiber 27 into reflected light of the wavelength band of R, reflected light of the wavelength band of G, and reflected light of the wavelength band of B, and outputs the three types of reflected light to detectors 87a, 87b, and 87c, respectively.

The detectors 87a, 87b and 87c are PD elements or the like configured to detect light intensities of the reflection lights in the R, G, and B wavelength bands, respectively. Signals of light intensities detected by detectors 87a, 87b, and 87c are outputted to A/D converters 88a, 88b, and 88c, respectively. The A/D converters 88a to 88c convert the analog signals of light intensities outputted from the detectors 87a to 87c to digital signals, and output the converted digital signals to the integrated control section 73.

The integrated control section 73 performs predetermined image processing on the digital signals from the A/D converters 88a to 88c to generate a subject image, and displays the subject image on the monitor 4.

Monochromatic light or a laser beam may be used as the illumination light.

Since the light scanning type endoscope 2 is equipped with any one of the small-diameter optical fiber scanning devices 10, 10A to 10K each performing efficient scanning irradiation at the rigid distal end portion 94 of the insertion section 91, the rigid distal end portion 94 has a small diameter and little invasive. Furthermore, since the optical fiber scanning devices 10 and 10A to 10K perform high-precision scanning irradiation, the optical scanning type endoscope 2 can obtain a good image. Furthermore, the optical scanning type endoscope 2 has low power consumption because the optical fiber scanning devices 10, 10A to 10K can be efficiently driven.

Needless to say, the present invention is not limited to the respective forgoing embodiments, and various modifications, combinations, and applications can be made without departing from the subject matter of the invention.

What is claimed is:

1. An optical fiber scanning device comprising:
   a housing having a cylindrical shape;
   an optical fiber that is arranged along a center axis of the housing and configured to emit light from a free end of the optical fiber;
   a magnet disposed on the optical fiber;
   four drive coils that are disposed in the housing and configured to drive the free end of the optical fiber by applying, to the magnet, a magnetic field generated by a received drive power signal; and
   four detection coils that are disposed in the housing and configured to output an induced electromotive force signal corresponding to variation of a magnetic field, wherein
   the drive power signal is controlled based on the induced electromotive force signal, and
   four coil assemblies each including any one of the drive coils and any one of the detection coils are disposed at rotationally symmetrical positions so as to interpose the optical fiber among the four coil assemblies.

2. The optical fiber scanning device according to claim 1, wherein the drive coils and the detection coils are planar spiral coils.

3. The optical fiber scanning device according to claim 2, wherein a center of the detection coil of each of the coil assemblies is arranged so as to be eccentric from a center of the drive coil of the coil assembly and overlap a winding portion of the drive coil of the coil assembly when each of the coil assemblies is viewed in plan view.

4. The optical fiber scanning device according to claim 3, wherein one end portion of the magnet is arranged on a line connecting centers of the two detection coils of the two coil assemblies arranged so as to face each other, and another end portion of the magnet is arranged on a line connecting centers of the two drive coils of the two coil assemblies arranged so as to face each other.

5. The optical fiber scanning device according to claim 1, wherein in each of the coil assemblies, the drive coil of the coil assembly is disposed on a first coil board, the detection coil of the coil assembly is disposed on a second coil board, and the first coil board and the second coil board are laminated.

6. The optical fiber scanning device according to claim 1, wherein in each of the coil assemblies, the drive coil of the coil assembly and the detection coil of the coil assembly are disposed on one coil board.

7. The optical fiber scanning device according to claim 6, wherein the coil board has a first principal surface and a second principal surface opposed to the first principal surface, and in each of the coil assemblies, the drive coil of the coil assembly is disposed on the first principal surface and the detection coil of the coil assembly is disposed on the second principal surface.

8. The optical fiber scanning device according to claim 6, wherein in each of the coil assemblies, the drive coil of the coil assembly and the detection coil of the coil assembly are disposed on a same principal surface of the coil board.

9. The optical fiber scanning device according to claim 1, wherein in each of the coil assemblies, at least part of the drive coil of the coil assembly or the detection coil of the coil assembly is constituted by a multilayer wiring plate.

10. The optical fiber scanning device according to claim 1, wherein in each of the coil assemblies, each of the drive coil of the coil assembly and the detection coil of the coil assembly is constituted by a multilayer wiring plate.

11. The optical fiber scanning device according to claim 1, wherein in each of the coil assemblies, a yoke formed of a soft magnetic body is disposed on the drive coil of the coil assembly and the detection coil of the coil assembly.

12. The optical fiber scanning device according to claim 1, wherein the drive power signal is controlled based on a correction signal in which influence on induced electromotive force by a magnetic field generated by the drive coil is canceled from the induced electromotive force signal.

13. An optical scanning type endoscope including an optical fiber scanning device at a rigid distal end portion of an insertion section, wherein
   the optical fiber scanning device comprises:
      a housing having a cylindrical shape;
      an optical fiber that is arranged along a center axis of the housing and configured to emit light from a free end of the optical fiber;
      a magnet disposed on the optical fiber;
      four drive coils that are disposed in the housing and configured to drive the free end of the optical fiber by applying, to the magnet, a magnetic field generated by a received drive power signal; and
      four detection coils that are disposed in the housing and configured to output an induced electromotive force signal corresponding to variation of a magnetic field,
      the drive power signal is controlled based on the induced electromotive force signal, and
      four coil assemblies each including any one of the drive coils and any one of the detection coils are disposed at rotationally symmetrical positions so as to interpose the optical fiber among the four coil assemblies.

14. An endoscope system comprising:
   an optical scanning type endoscope including an optical fiber scanning device;
   a power supply configured to output a drive power signal;
   a correcting circuit configured to output a correction signal in which influence on induced electromotive force by a magnetic field generated by a drive coil is cancelled from an induced electromotive force signal; and
   a controller configured to control the power supply based on the correction signal, wherein
   the optical fiber scanning device comprises:
   a housing having a cylindrical shape;
   an optical fiber that is arranged along a center axis of the housing and configured to emit light from a free end of the optical fiber;
   a magnet disposed on the optical fiber;
   four drive coils that are disposed in the housing and configured to drive the free end of the optical fiber by applying, to the magnet, a magnetic field generated by a received drive power signal; and four detection coils that are disposed in the housing and configured to output an induced electromotive force signal corresponding to variation of a magnetic field, the drive power signal is controlled based on the induced electromotive force signal, and four coil assemblies each including any one of the drive coils and any one of the detection coils are disposed at rotationally symmetrical positions so as to interpose the optical fiber among the four coil assemblies.

* * * * *